(12) United States Patent
Chen et al.

(10) Patent No.: US 9,217,162 B2
(45) Date of Patent: Dec. 22, 2015

(54) METHOD AND APPARATUS FOR ANAEROBIC DIGESTION FOR CROP STALK

(75) Inventors: Yiliang Chen, Dongying (CN); Jianzhong Zhao, Dongying (CN); Rongjun Li, Dongying (CN); Shaopeng Zhang, Dongying (CN); Taitao Wang, Dongying (CN); Tong Wang, Dongying (CN); Zhiguo Chen, Dongying (CN)

(73) Assignee: Shengli Oilfield Shengli Power Machinery Co., Ltd., Dongying (CN)

( * ) Notice: Subject to any disclaimer, the term of this patent is extended or adjusted under 35 U.S.C. 154(b) by 812 days.

(21) Appl. No.: 13/055,426

(22) PCT Filed: Jul. 21, 2009

(86) PCT No.: PCT/CN2009/072844
§ 371 (c)(1),
(2), (4) Date: Jun. 15, 2011

(87) PCT Pub. No.: WO2010/009668
PCT Pub. Date: Jan. 28, 2010

(65) Prior Publication Data
US 2011/0281254 A1    Nov. 17, 2011

(30) Foreign Application Priority Data

Jul. 21, 2008  (CN) .......................... 2008 1 0138810
Jul. 21, 2008  (CN) .......................... 2008 1 0138811
Jul. 21, 2008  (CN) .......................... 2008 2 0026513

(51) Int. Cl.
| | |
|---|---|
| C12P 5/02 | (2006.01) |
| C12M 1/107 | (2006.01) |
| C12M 1/16 | (2006.01) |
| C12M 1/00 | (2006.01) |
| C12M 1/33 | (2006.01) |
| C12M 1/06 | (2006.01) |
| C12M 1/34 | (2006.01) |
| C12M 1/02 | (2006.01) |

(52) U.S. Cl.
CPC ............... *C12P 5/023* (2013.01); *C12M 21/04* (2013.01); *C12M 21/16* (2013.01); *C12M 23/58* (2013.01); *C12M 27/02* (2013.01); *C12M 41/12* (2013.01); *C12M 41/18* (2013.01); *C12M 45/02* (2013.01); *Y02E 50/343* (2013.01)

(58) Field of Classification Search
CPC ............................. C12P 5/023; C12M 21/04
See application file for complete search history.

(56) References Cited

U.S. PATENT DOCUMENTS 6,299,774 B1 * 10/2001 Ainsworth et al. ........... 210/603
7,163,629 B2 * 1/2007 Abu-Orf et al. ............... 210/603

(Continued)

FOREIGN PATENT DOCUMENTS

| CN | 1896219 | 1/2007 |
| CN | 101215520 | 7/2008 |
| WO | WO 2006/107696 | 10/2006 |

OTHER PUBLICATIONS

International Search Report for Application No. PCT/CN2009/072844 dated Oct. 16, 2009.

(Continued)

*Primary Examiner* — Jonathan Hurst
(74) *Attorney, Agent, or Firm* — Merchant & Gould P.C.

(57) ABSTRACT

This disclosure discloses a process and an anaerobic digestion system for crop stalk/straw. The process in one example comprises (A) Feeding, (B) Heating and Digestion at the set temperature, (C) Discharging of Biogas, Sludge and Effluent. The system in one example comprises (I) High Solid Content Digester (II) Hydro-Circulation Digester and (III) Stalk/Straw Feeder. Steps (A), (B) and (C) are accomplished in the devices (I) and (II).

4 Claims, 1 Drawing Sheet

(56) References Cited

U.S. PATENT DOCUMENTS

| | | | | |
|---|---|---|---|---|
| 7,781,194 B2* | 8/2010 | Weidele | .................. | 435/166 |
| 2002/0102673 A1* | 8/2002 | Zhang et al. | .................. | 435/167 |
| 2006/0256645 A1* | 11/2006 | Jensen et al. | .................. | 366/131 |
| 2009/0305379 A1* | 12/2009 | Johnson et al. | .................. | 435/170 |

OTHER PUBLICATIONS

Chen et al. "Research progress and prospect on producing biogas from crop straws" *Transactions of Agricultural Engineering.* vol. 23. No. 3. Mar. 2007. pp. 279-282.

\* cited by examiner

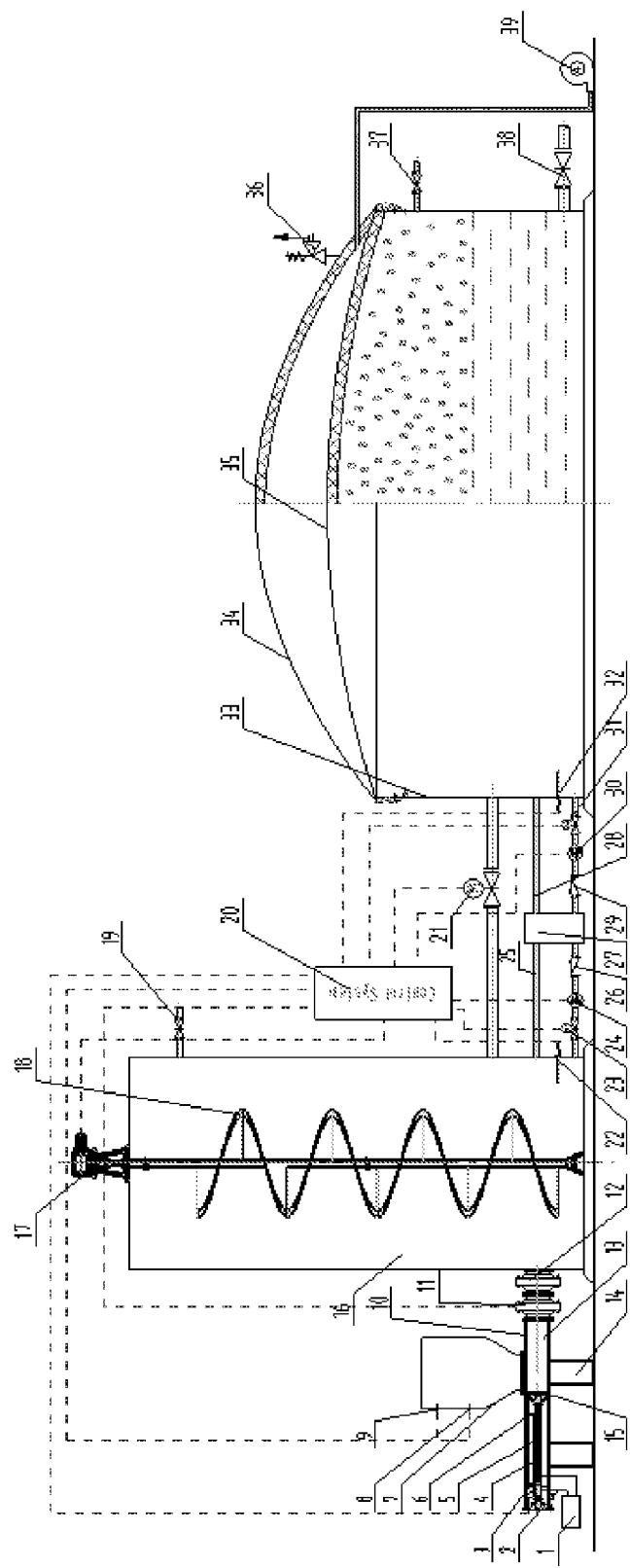

US 9,217,162 B2

METHOD AND APPARATUS FOR ANAEROBIC DIGESTION FOR CROP STALK

This application is a National Stage Application of PCT/CN2009/072844, filed 21 Jul. 2009, which claims benefit of Serial No. 200810138811.2, Serial No. 200810138810.8, and Serial No. 200820026513.X, filed 21 Jul. 2008 in China and which applications are incorporated herein by reference. To the extent appropriate, a claim of priority is made to each of the above disclosed applications.

BACKGROUND

This disclosure relates to a process and a system of anaerobic digestion for agricultural biomass waste, livestock waste and industrial wastewater in the presence of anaerobic microorganism, and in particular, relates to the process and system combining the high solid content digestion and the hydro circulation digestion. In this system the material and liquid in the enclosed vessels always flow at one direction, and the system is sealed to prevent other foreign medium going into the system.

Currently, the common anaerobic digestion methods and devices are Complete Stirred Tank Reactor process (CSTR), Anaerobic contact process Reactor, Up-flow Anaerobic Sludge Bed (USAB) and Up-flow Solids Reactor (USR). Those have the following disadvantages: (a). These devices are only suitable for livestock manure and but not to digest crop materials such as stalk or straw due to excessive high carbon & nitrogen ratio in the stalk in comparison with the required carbon & nitrogen ratio by anaerobic digestion; (b). Most of above mentioned devices use internal heating, consequently, such digester gets corrosive easily with bad sealing, and therefore to interfere the growth of aerobic bacteria; (c). Such devices are complicated and a gas storage tank is also required, therefore, these need much large land to install but also with long down time for maintenance; (d). Due to interval feeding and discharging, such devices have to start frequently causing low efficiency; (e). Feedstock generally is fed into the digester from the top, and it is difficult to mix the feedstock well enough inside the digester, therefore, causing caking at top surface of the liquid level; and (f). Higher investment will be needed due to more accessories and high operation cost.

Currently used pneumatic conveying system has some disadvantages: (a) The pneumatic conveying system is merely suitable to transport these materials that are not vulnerable to agglomeration though the system can be used to transport the materials in an enclosed channel; (b) Due to the bad seal, air may be mixed in the system entering the digesters.

SUMMARY

Certain examples given in the present disclosure provide a type of a process and an anaerobic digestion system particularly for crop stalks/straws, and also the process and device is applicable for livestock wastes and other waste materials. This invention fills this gap in the anaerobic digestion device for crop stalk/straw and expands the applicability and adaptability of the anaerobic digestion. Using an innovative stalk feeder driven by hydraulic power can transport the material in an enclosed condition, featuring optimal sealing, low energy consumption and excessive over-load operation. The feeder overcomes the disadvantages in the existing technology.

A process and an anaerobic digestion system for crop stalk/straw include the following procedures in such order: (A) Feeding, (B) Heating—and keeping the anaerobic digestion at the set temperature, (C) Discharging. The process (A), (B) and (C) are accomplished through the devices (I) and (II). In step (A), the crushed or smashed crop stalk/straw is pushed into the digestion device from its bottom through the feeder (III). After being fermented or digested in the device (I), the feedstock flows freely into device (II). Step (B) is accomplished by checking the temperatures in the digesters by the temperature sensors mounted on the devices (I) and (II). When the digester temperature is below the set value, the control system of the digesters starts automatically to send the mixture of biomass and liquid through the circulation pump into the heat exchanging mechanism; and the heated flow then goes back to the digesters. This step is repeated in the digester (II) to keep the digester at the set temperature while material inside the digester (II) is mechanically agitated simultaneously. With being stirred by a mixer, feedstock in device (I) gets mixed sufficiently with anaerobic organisms. In Step (C) the material inside the digester vessel (or pressure vessel) (33) is digested continuously and converted into biogas, sludge and effluent, which run out through its individual outlet.

The feedback being pumped out of the digester into the heat exchanging mechanism is heated by the external circulation heat in the step (B). The feedstock is agitated under the turbulence effect that is created while feedback is pumped out from the digester into heat exchanging mechanism. Furthermore, feedstock in device (I) is stirred by mechanical method in conjunction with hydropower available in the inlet and outlet of the heat exchanger. The biogas from the biogas outlet in digester is delivered to its downstream uses, effluent runs out of the effluent outlet and sludge is discharged from the outlet at the bottom of the digester.

Certain examples given in the present disclosure provide a process and an anaerobic digestion system for crop stalks/straws. This system is constituted with the automatic control and the heat exchanging mechanism outside the digester vessels. The examples given in the present disclosure achieve digestion of crop stalk/straw effectively by eliminating the disadvantages in the existing technology. Certain examples given in the present disclosure provide a special system of anaerobic digestion for crop stalk/straw available to produce biogas for household consumption or for electricity generator sets.

A process and an anaerobic digestion system for crop stalks/straws in certain examples given in the present disclosure include (I) High Solid Content Digester (II) Hydro-Circulation Digester and (III) Stalk/Straw Feeder. The device (I) consists of a digester vessel (or pressure vessel) (16), a reducing gearbox (17), a mixer (18), a heat exchanging mechanism (27), a gate valve (11), a temperature sensor (22) and a control system (20). The digester vessel is furnished with a reducing gearbox on its top. The gearbox is attached to a mixer. At one side adjacent to the digester vessel, the safety valve (12), stalk gate valve (11), stalk feeder are arranged in sequence; at another side, the electric valve (23), feedstock circulation pump (26), check valve (24), heat exchanging mechanism (27), feedstock returning pipes (25) and temperature sensor (22) are connected in sequence at the bottom of the digester vessel. A feedstock discharge outlet is located at the center of the digester vessel and a biogas outlet (19) is at its top. The control system (20) mounted outside of the digester vessel (16) is wired to the gearbox (17), electric valve (23), circulation pump (26) and temperature sensor (22).

The device (II) consists of a digester vessel (33), a heat exchanging mechanism (27), a feedstock inlet (21), interior cover (35), exterior cover (34), safety valve (36), feedstock output valve (38), a blower (39), a temperature sensor (32), electric valve (31), a circulation pump (29), a check valve (30)

and a control system (20). The heat exchanging mechanism (27) and feedstock input valve (21) are mounted adjacent to the digester vessel on one side. The biogas outlet valve (37) and feedstock output valve (38) are arranged on another side of the digester vessel. At the top of the digester vessel is the interior and exterior covers (34 and 35) in sequence. Exterior cover (35) is installed with a safety valve (36). Between the interior and exterior covers there is an air pocket, which is connected to the blower and pipes. A temperature sensor (32) is arranged at the lower part of the digester vessel. The control system (20) mounted outside the digester vessel (33) is wired to the circulation pump (29), electric valve (31), temperature sensor (32) and blower (39).

The stalk/straw feeder (III) includes a hopper (7), a support (14), a hydraulic system and a control system (20). The hydraulic system consists of a hydraulic cylinder (3), a hydraulic pump station (1), hydraulic pipelines (2), a piston (15), a piston rod (5) and a feedstock input passage (13). The hopper is square shaped on its upper section and conical shaped its lower bottom part. The hopper has a high-level sensor and is connected to transporting part driven by the hydraulic system at its lower section. The hydraulic system and the level sensor are wired to the control system to provide the feeding function to the digester.

Hereinto, the mixer for the digester vessel of device (I) is structured in helical rotation. The mixer is connected to the gearbox at the top and inner bottom of digester vessel. The heat exchanging mechanism outlet is connected to the feedstock returning pipes open to the digester vessel. The heat exchanging mechanism inlet is connected to the backstop valve, electric valve and circulation pump. The electric valve of feedstock outlet mounted on the digester vessel is wired to the control system. The heat exchanging mechanism is open to the digester vessel through the related pipelines, backstop valve, electric valve and circulation pump. The device (I) is structured as that its diameter is less than its height. The device (II) is structured as that its diameter is larger than its height. The sensors are installed at the high and low positions, respectively. The hopper has a high-level sensor and is connected to transporting part driven by the hydraulic system at its lower section. The limit sensor and limit switch, which are wired to the control system, are installed in the hydraulic cylinder to control the piston to move back and forward. The the control system is a PLC controller to collect and process the signals from the mounted sensors and converters.

In comparison with the current existing technology, certain examples given in the present disclosure have one or more of the following advantages:

1) It is suitable for transporting raw materials such as crop stalk/straw, granules or other soft solid-liquid mixture.
2) Feedstock is transported in an enclosed condition without other medium required. Moreover, a feedstock level sensor is arranged in the hopper. As the feedstock level is below the defined value, the other feeding device is triggered to feed materials in to the hopper. This can prevent air getting into the digester vessel while the hopper is the absence of feedstock.
3) The feeder is driven by the hydraulic power. A safety valve is applied in the system to prevent the devices from damage due to overload.
4) The digesters are suitable for a broad range of raw materials including different sewage animal waste, although the examples given in the present disclosure are primarily designed for crop stalk/straw.
5) The feedstock is pushed into the digester vessel from the bottom and, simultaneously, is agitated by a mechanical mixer and liquid jet flows in and out from the heat exchanging mechanism. The feedstock is mixed sufficiently and thus caking on the liquid surface does not occur. Feeding from the top of the digester vessel will let the feedstock sitting on the top of liquid surface causing agglomeration due to uneven mixture.
6) The heated feedstock flow from the heat exchanger acts as the water jet to stir the liquid inside the digester vessel. This will increase the digestion efficacy and reduce the operation cost.
7) The feedstock is heated by the heat source coming from circulation heat outside the digester vessel. There is no inside pipeline in the digester vessel. It is easy to perform the maintenance work and avoid the possible corrosion.
8) No other medium like water or additives is wanted in this process.
9) The digester vessels are also used as gas storage tanks, thus less investment and land are required.
10) The biogas storage system is constituted without water seal, oil seal and other movable parts, so the system will not suffer from freezing during cold weather.
11) The gas storage system is built without rail, elevating piston and weight balance mounted.
12) The system has simple structure featuring convenient maintenance, high reliability, less downtime and low operating cost.

BRIEF DESCRIPTION OF THE DRAWINGS

The following drawing figure is illustrative of embodiments of systems and methods described below and is not meant to limit the scope of the disclosure in any manner, which scope shall be based on the claims appended hereto.

FIG. 1 is a schematic illustration of the structure of an exemplary system of digestion according to one aspect of the present disclosure.

DETAILED DESCRIPTION OF ILLUSTRATIVE EMBODIMENTS

A process of crop stalk/straw anaerobic digestion for biogas is included with the following procedures in such order: (A) Feeding, (B) Heating—and keeping the anaerobic digestion at the set temperature, (C) Discharging biogas, sludge and effluent. The process (A), (B) and (C) are accomplished through the devices (I) and (II). In step (A), the crushed or smashed crop stalk/straw is pushed into the digestion device (I) from its bottom through the feeding mechanism (III). After being digested in the device (I), the feedstock flows freely into the devices (II). As for step (B), temperature in digester vessels is detected by the temperature sensors mounted on the devices (I) and (II). When digester vessel temperature is below the set value, the control systems for the devices start automatically to pump the feedstock out of the digester vessels into the heat exchanging mechanisms through the circulation pumps and then back to the digester vessel after temperature rises. This step is repeated in devices (II), and feedback inside the digester vessel is agitated simultaneously. With being stirred by a mixer, feedstock in devices (I) gets mixed sufficiently with anaerobic organism. In step (C), the feedstock is digested continuously and converted into biogas, sludge and effluent, which is discharged or drained out through its individual outlet.

The feedback being pumped out of the digester vessel into the heat exchanging mechanism is heated by the external circulation heat in the step (B). The feedstock is agitated under the turbulence effect that is created while feedback is pumped out from the digester vessel into heat exchanging mechanism. Furthermore, feedstock in device (I) is stirred by mechanical method in conjunction with hydropower available in the inlet and outlet of the heat exchanger. The biogas from the biogas outlet in digester vessel is delivered to its downstream uses, effluent runs out of the effluent outlet and sludge is discharged from the outlet at the bottom of the digester vessel.

Certain examples given in the present disclosure provide a process and an anaerobic digestion system for crop stalks/straws. This system is constituted with the automatic control and the heat exchanging mechanism outside the digester vessels. The examples make achieve digestion of crop stalk/straw effectively by eliminating the disadvantages in the existing technology. This disclosure provides a special system of anaerobic digestion for crop stalk/straw available to produce biogas for household consumption or for electricity generator sets.

A process and an anaerobic digestion system for crop stalks/straws in certain examples given in the present disclosure include (I) High Solid Content Digester (II) Hydro-Circulation Digester and (III) Stalk/Straw Feeder. The device (I) consists of a digester vessel (16), a reducing gearbox (17), a mixer (18), a heat exchanging mechanism (27), a gate valve (11), a temperature sensor (22) and a control system (20). The digester vessel is furnished with a reducing gearbox on its top. The gearbox is attached to a mixer. At one side adjacent to the digester vessel, the safety valve (12), stalk gate valve (11), stalk feeder are arranged in sequence; at another side, the electric valve (23), feedstock circulation pump (26), check valve (24), heat exchanging mechanism (27), feedstock returning pipes (25) and temperature sensor (22) are connected in sequence at the bottom of the digester vessel. A feedstock discharge outlet is located at the center of the digester vessel and a biogas outlet (19) is at its top. The control system (20) mounted outside of the digester vessel (16) is wired to the gearbox (17), electric valve (23), circulation pump (26) and temperature sensor (22).

The device (II) consists of a digester vessel (33), a heat exchanging mechanism (27), a feedstock inlet (21), interior cover (35), exterior cover (34), safety valve (36), feedstock output valve (38), a blower (39), a temperature sensor (32), electric valve (31), a circulation pump (29), a check valve (30) and a control system (20). The heat exchanging mechanism (27) and feedstock input valve (21) are mounted adjacent to the digester vessel on one side. The biogas outlet valve (37) and feedstock output valve (38) are arranged on another side of the digester vessel. At the top of the digester vessel is the interior and exterior covers (34 and 35) in sequence. Exterior cover (35) is installed with a safety valve (36). Between the interior and exterior covers there is an air pocket, which is connected to the blower and pipes. A temperature sensor (32) is arranged at the lower part of the digester vessel. The control system (20) mounted outside the digester vessel (33) is wired to the circulation pump (29), electric valve (31), temperature sensor (32) and blower (39).

The stalk/straw feeder (III) includes a hopper (7), a support (14), a hydraulic system and a control system (20). The hydraulic system consists of a hydraulic cylinder (3), a hydraulic pump station (1), hydraulic pipelines (2), a piston (15), a piston rod (5) and a feedstock input passage (13). The hopper is square shaped on its upper section and conical shaped its lower bottom part. The hopper has a high-level sensor and is connected to transporting part driven by the hydraulic system at its lower section. The hydraulic system and the level sensor are wired to the control system to provide the feeding function to the digester.

The mixer for the digester vessel of device (I) is structured in helical rotation. The mixer is connected to the gearbox at the top and inner bottom of digester vessel. The heat exchanging mechanism outlet is connected to the feedstock returning pipes open to the digester vessel. The heat exchanging mechanism inlet is connected to the backstop valve, electric valve and circulation pump. The electric valve of feedstock outlet mounted on the digester vessel is wired to the control system. The heat exchanging mechanism is open to the digester vessel through the related pipelines, backstop valve, electric valve and circulation pump. The device (I) is structured as that its diameter is less than its height. The device (II) is structured as that its diameter is larger than its height. The sensors are installed at the high and low positions, respectively. The hopper has a high-level sensor and is connected to transporting part driven by the hydraulic system at its lower section. The limit sensor and limit switch, which are wired to the control system, are installed in the hydraulic cylinder to control the piston to move back and forward. The the control system is a PLC controller to collect and process the signals from the mounted sensors and converters.

During operation, solid particles in the hopper (7) flow into the feed passage (13) embedded in the casing (10) under action of gravity. The control system (20) sends signal to the hydraulic station (1) to let hydraulic fluid flow into the left chamber of the hydraulic cylinder (4). Then, the hydraulic cylinder drives piston (15) to move forward and forces the solid particles in the feeding passage to go forward. While moving forward, solid particle is stopped by the stalk gate valve (11) and an enclosed space is formed in this area. At this time, the stalk gate valve (11) is closed and the piston rod (5) keeps moving forward pressing the solids continuously. While pressure in the passage rises, the control system (20) collects pressure data from the stalk passage and stores these values. When pressure reaches the defined value of the digester vessel, the control system (20) opens the stalk valve (11). Piston (15) continues to push the solids into the digester vessel. When the piston (15) reaches the designed maximum position (6), the control system (20) closes the stalk valve, simultaneously. The control system (20) drives the hydraulic pump station to have hydraulic fluid flow into the right chamber of the hydraulic cylinder. Driven by the hydraulic cylinder (4), piston (15) begins to move back. When the piston comes back to certain position, the hopper (7) begins to load feedstock. When the piston (15) moves at the minimum position (3), this feeding activity stops. Under the action of the control system (20), the piston rod (5) moves forward driven by hydraulic cylinder (4). In the hopper (7), feedstock level sensors (8) and (9) are installed. When the feedstock level is below the minimum value, other facilities outside the digestion system start to feed the system with feedstock. Keeping the hopper (7) with minimal level of feedstock will prevent air getting into the digester vessel. When the stalk gate valve (11) opens, piston (15) pushes the solids into the digester vessel to complete its feeding cycle.

Through the stalk feeder, crushed or smashed stalk/straw is pushed into the digester vessel (16) from the bottom. The stalk gate valve (11) (as a special part) assists the feeder during the whole process of feeding to prevent feedstock in the digester vessel (16) flowing back. The safety valve (12) guarantees to stop the feedstock inside the digester vessel flowing back to the feeder if the stalk valve fails. After being stirred by the mixer (18), incoming feedstock is mixed well enough with both the feedstock inside and the anaerobic organism in the digester vessel (16) for better digestion. Connected to the reducing gearbox (17), the mixer (18) rotates at low speed. In the process of the anaerobic digestion, the temperature sensor (22) detects feedstock temperature inside the digester vessel (16). When temperature is below the setting value, the control system (20) starts the feedstock circulation pump (24) to pump feedstock into the heat exchanging mechanism (27). After the feedstock temperature rises in the heat exchanging mechanism (27), the heated feedstock returns to the digester vessel through the feedstock returning pipes (25) under the pressure of feedstock circulation pump (24), therefore, to heat the feedstock inside the digester vessel. While the temperature in the digester vessel (16) reaches the setting value, the feedstock circulation pump (24) stops. The material inside the digester vessel is treated by anaerobic digestion at the set temperature. In addition, feedstock is also stirred while it flows out and back to the digester vessel under the action of feedstock circulation pump. The sludge and effluent from the digester vessel (16) will flow into the digester vessel (33) through valve (21) that is controlled by the control system for further digestion. During the process of the anaerobic digestion, temperature sensor (32) detects feedstock temperature inside the digester vessel (33). When temperature is below the set value, the control system (20) starts the feedstock circulation pump (30) to pump feedstock into the heat exchanging mechanism (27). After the feedstock temperature rises in the heat exchanging mechanism (27), the heated feedstock returns to the digester vessel through the feedstock returning pipes (28) under the action of feedstock circulation pump (30). The feedstock is mixed while it is being heated. After digestion, the sludge and effluent are drained out through the electric valve (38). The biogas produced during digestion discharges from the biogas outlet (19) and (37) to the downstream users or to generate electricity.

Those skilled in the art will recognize that the methods and devices of the present disclosure may be implemented in many manners and as such are not to be limited by the foregoing embodiments and examples. Moreover, the scope of the present disclosure covers conventionally known manners for carrying out the described features and functions, as well as those variations and modifications that may be made to the materials and shapes of the components described herein as would be understood by those skilled in the art now and hereafter.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure. Numerous other changes may be made that will readily suggest themselves to those skilled in the art and which are encompassed in the spirit of the invention disclosed and as defined in the appended claims.

We claim:

1. A process for fermenting crop stalk/straw to produce biogas, including, in order:
   (A) intaking feedstock;
   (B) heating the feedstock and maintaining the temperature of the feedstock anaerobic digestion of the feedstock; and
   (C) discharging biogas, sludge and effluent,
   wherein (A), (B) and (C) are carried out in a system comprising:
   (I) a High Solid Content Digester, comprising a digester vessel having a height greater than diameter and defining a stalk gate in a bottom portion of the vessel, a helical mixer disposed in the vessel and adapted to agitate crushed or smashed crop stalk/straw, and a temperature sensor at the bottom portion,
   (II) a Hydro-Circulation Digester comprising a digester vessel containing no mixer and having a diameter greater than height, circulation pump, a feedstock intake valve mounted adjacent to the Hydro-Circulation digester vessel and adapted to permit a sludge and effluent from the High Solid Content Digester vessel to flow into the Hydro-Circulation digester vessel and a temperature sensor mounted in a bottom portion of the vessel, and
   (III) a feeder comprising a hopper adapted to provide crushed or smashed crop stalk/straw into the High Solid Content Digester vessel through the stalk gate, and
   (IV) a heat exchanger and pipes connecting both digester vessels to the heat exchanger for heating feed stock circulated from and back to the respective vessels,
   wherein:
   step (A) comprise pushing crushed or smashed crop stalk/straw into the digester (I) from its bottom through the feeder (III) and the gate, and transporting the feedstock into the digester (II) after the feedstock has been digested in the digester (I),
   step (B) comprises:
      detecting the temperatures in the digesters using the temperature sensors mounted in the bottom portions of the digesters (I) and (II), respectively,
      when temperatures in the respective digesters are below respective set values, using a control system to automatically start respective circulation pumps to pump the feedstock out of the respective digesters into a heat exchanging mechanism and then back to the respective digester vessels after the temperatures rises to their respective desired values,
      repeating the above portions of step (B) in digester (II), and agitating the feedback inside the digester (II) simultaneously,
      using a mixer, mixing feedstock with anaerobic organism in the digester (I); and
   step (C) comprises digesting the feedstock continuously, thereby converting it into biogas, sludge and effluent, and
   discharging the biogas, sludge and effluent from at least one of the digesters through a biogas outlet, sludge outlet and effluent outlet, respectively.

2. The process of claim 1, wherein the feedback is heated by an external heat exchanger after being pumped out of at least one of the digesters into the heat exchanging mechanism.

3. The process of claim 1 or 2, wherein the feedback is agitated under the effect of turbulence which takes place while feedback is pumped in or out while being heated in the heat exchanging mechanism, wherein the feedstock in the digester (I) is stirred by both mechanical and hydraulic methods.

4. The process of claim 1, wherein the biogas from the biogas outlet is delivered to its downstream uses, the effluent is discharged through an effluent outlet and sludge is discharged from the outlet at the bottom of the digester.

* * * * *